United States Patent [19]

Southard

[11] Patent Number: 4,683,133
[45] Date of Patent: Jul. 28, 1987

[54] METHOD FOR TREATING PERIODONTAL DISEASE

[75] Inventor: G. Lee Southard, Fort Collins, Colo.

[73] Assignee: Vipont Laboratories, Inc., Ft. Collins, Colo.

[21] Appl. No.: 767,606

[22] Filed: Aug. 20, 1985

[51] Int. Cl.$^4$ .................. A61K 7/16; A61K 33/30; A61K 31/44
[52] U.S. Cl. .................. 424/49; 424/145; 514/279; 514/280; 514/902
[58] Field of Search .................. 424/49, 58, 145; 514/279, 280, 902

[56] References Cited

U.S. PATENT DOCUMENTS 4,060,600 11/1977 Vit .................. 424/53
4,145,412 3/1979 Ladanyi .................. 424/58
4,335,110 6/1982 Collins .................. 424/58
4,376,115 3/1983 McCrorey .................. 424/145
4,406,881 9/1983 Ladanyi .................. 424/145
4,489,750 12/1984 Wehring .................. 137/496

OTHER PUBLICATIONS

Chem. Abst. 96: 129,814(e)(1982)–Ladanyi.
Chem. Abst. 102: 201040(m)(1985)–Dzink et al.

Primary Examiner—Douglas W. Robinson
Attorney, Agent, or Firm—Eric P. Schellin

[57] ABSTRACT

A self-administerable method of treating periodontal disease by providing a dilute aqueous solution of a non-toxic benzo-c-phenanthridine salt, pumping the solution through an orifice to provide a pulsating jet stream that is capable of penetrating directly into the periodontal pockets associated with periodontal disease, and applying the jet stream to diseased gingival tissue and into the periodontal pockets.

7 Claims, No Drawings

METHOD FOR TREATING PERIODONTAL DISEASE

BACKGROUND OF THE INVENTION

The present invention relates to a method for treating diseases which affect the supporting tissues of the teeth, and particularly to a method for treating periodontitis.

Benzo-c-phenanthridine alkaloids can be extracted from plants of the families Papaveracease, Fumariaceae, and Berberidaceae. Some of the plants of these families include *Sanguinaria canadensis, Macleaya cordata, Bocconia frutescens, Carydalis sevctcozii, C. ledebouni, Argemone mexicanus,* and *Chelidonium majus.* Among the most important benzo-c-phenanthridine alkaloids obtained from these plants are sanguinarine, chelirubine, macarpine, allocryptopine, protopine, hemochelidonene, sanguilatine, sanguirubine, and chelerythrine.

The best known of these alkaloids is sanguinarine, which has previously been extracted from the *Sanguinaria canadensis* plant, otherwise known as bloodroot, teterwort, redroot, puccoon, etc., a perennial herb native to North America. The Sanguinaria plant and its juices have been used for various purposes in pre-historic and historic times. The plants has been used, in particular, as a folk remedy. The plant had generally been used whole, either undried (fresh) or dried. The usual procedure is to powder the dried plant and mix it with a carrier. This folk remedy has been tried for such condition as asthma, bronchitis, dysentery, ringworm, and a substantial list of other ailments.

The pure chemicals sanguinarine, chelerythrine, protopine, chelerubine, berberine, chelilutine, sanguilatine, macarpine, sanguirubine, and allocryptopine can be isolated from plants other than Sanguinaria. They are also available, although rarely, from some chemical supply houses. Semi-purified forms of the alkaloids are commercially available, and these are generally referred to as sanguinarine nitrate and sanguinarine sulfate. These "salts" are the salts of the mixed alkaloids of the plant Sanguinaria: mainly sanguinarine, chelerythrine, and protopine. While few references can be found in the literature regarding the usage of any of the pure benzophenanthridine alkaloids, plants containing such compounds have been used for a wide variety of medical ailments.

The alkaloid sanguinarine in solution has been shown to have some antifungal and antiprotozoan properties. The sanguinarine is applied as an emulsion topically to fungal infections. The antibacterial activity of sanguinarine has been found to vary with that attached radicals, and various salts of sanguinarine have been shown to have some activity. The hydrochloride and the sulfate salts have been found to have some activity against certain bacteria at certain concentrations. Sanguinarine nitrate is reposted to have some bacteriostatic action against various types of bacteria.

An early patent, U.S. Pat. No. 209,331, discloses the use of bloodroot, zinc chloride, and kerosene oil in equal proportions for treating open sores. U.S. Pat. No. 433,257 describes a salve of pulverized bloodroot, armenian bole, powdered rosin, lard, and Stockholm tar for use in the treatment of piles. U.S. Pat. No. 2,344,830, discloses the use of a mixture of zinc chloride, stibnite, and bloodroot to fix and outline diseased tissue for excision by surgery.

Several more recent patents have disclosed the use of extracts of Sanguinaria for treating the oral cavity for conditioning oral tissue as well as in preventing and treating gingivitis, periodontitis, and mouth odors. Some of the patents describing the use of Sanguinaria extracts as antimicrobial agents as well as mouth treating agents are U.S. Pat. No. 4,145,412; U.S. Pat. No. 4,406,881; U.K. Pat. No. 2,042,336; U.S. Pat. No. 4,376,115; German Offen. No. 2,907,406; Belgian No. 888,843. The use of sanguinarine with thiophosphoric acid in various animal and human neoplasms is shown in French Pat. Nos. 70-22029 and 2,159,972.

In the past, the active ingredients were extracted from the plant material by extracting the comminuted plant material with methanol, filtering the liquid extract obtained, evaporating the extract to dryness, dissolving the dried residue in chloroform, acidifying the chloroform extract, filtering the acidified extract, evaporating it to dryness, and dissolving the dried residue in glycerine for mixing with a carrier.

Periodontitis, or pyorrhea, is a disease affecting the supporting tissues of the teeth including the gingiva, the membrane lining the sockets in which the teeth lie, and the bones surrounding the teeth. The disease may initially be associated with conditions of constant irritation of the gingiva by dental calculus, food impaction, poor dental restoration, traumatic occlusion, or chemical irritants.

When normal, the gums are pink and resilient, and heal promptly when injured. The gums, however, may be seriously harmed by deposits of dental calculus (tartar), a combination of mineral and bacteria found in the mouth. The bacteria associated with tartar can secrete enzymes and endotoxins which can irritate the gums and cause inflammatory gingivitis. As the gums become increasingly irritated by this process they have a tendency to bleed, lose their toughness and resiliency, and separate from the teeth, leaving periodontal pockets in which debris, secretions, more bacteria, and toxins further accumulate. It is also possible for food to accumulate in these pockets, thereby providing nourishment for increased growth of bacteria and procuction of endotoxins and destructive enzymes. The pus that forms in the process is capable of destroying gum and bone tissue. A variety of bacteria are generally found to be present during the active stages of periodontal disease. Such organisms as streptococci, staphylococci, pneumococci, and the like, are usually present, and are found in the purulent discharge as well as in the involved tissue, and may be absorbed into the general system through the lymphatics or venous blood stream.

The progression of the pyorrhetic process usually begins with gingivitis, initiating at the margins of the gums, in which the gingiva become more tender and sensitive, and appear flabby, inflamed, and swollen. Periodontal pockets become apparent, and infection takes place in these pockets. Because the periodontal pockets cannot be cleaned by brushing or the use of dental floss, infection becomes progressive and constant. A purulent or toxic discharge is common from the affected tissues, with which may be associated an abnormal taste and odor in the mouth.

The periodontal disease may gradually involve the deeper periodontal tissues until all the supporting tissues of the teeth, including bone, are affected. When the pyorrheic process has proceeded to the stage of destruction of the periodontal tissues, the teeth become loosened, and are usually lost in the most advanced stages of the disease. An additional adverse effect on the general well being of the affected individual is the potential for absorption of a considerable amount of toxic prurulent or bacterial matter into the general circulation.

Although pyorrhea is generally considered curable in the early stages, when treated by a dentist, the most effective coventional treatment has been preventive, involving strict oral hygiene and periodic dental prophylaxis. Methods of treatment of persons who are already affected by the disease include regular calculus removal by the dentist, grinding off rough dental surfaces, surgical removal of diseased gingival tissue, and opening and trimming of periodontal gingival pockets.

However, conventional methods of treatment are not entirely satisfactory, and periodontitis continues to be a principal dental disease and a major case of the loss of teeth. A relatively simple method for treating periodontitis which would be effective in controlling the disease would be very desirable. In addition, such a method which could be employed by individual patients in self medication on a regular basis would be most desirable.

SUMMARY OF THE INVENTION

The present invention is directed to a method for treating periodontal disease. The method may be self-administered by an individual affected by the disease. The method comprises providing a dilute aqueous solution of a nontoxic benzo-c-phenanthridine alkaloid salt and mixtures thereof, and pumping the solution through an orifice to provide a pulsating jet stream of the solution which is capable of penetrating directly into the periodontal pockets associated with periodontal disease. In the treatment method, the pulsating jet stream of aqueous benzo-c-phenanthridine salt thus provided is applied to the diseased gingival tissues and into the periodontal pockets.

In use, the mineral acid salt of the desired benzo-c-phenanthridine alkaloid is dissolved in either deionized water or C1–C6 alcohols, glycerine, propylene glycol, petrolatum, or other organic solvents at 70 degrees C. Zinc chloride, if it is used, is added to the above solution at this time. The preparations generally contain about 0.01% and up to 10% by weight of the benzo-c-phenanthridine alkaloid salt, and from about 0% to about 35% by weight of zinc chloride, with the remainder being the solvent.

DETAILED DESCRIPTION OF THE INVENTION

An example of a basic preparation for use in aqueous solution for treating periodontal disease is as follows:

EXAMPLE I

| Sanguinarine chloride | 0.3% |
| glycerine, USP | 64.7% |
| zinc chloride | 35.0% |

EXAMPLE II

Other benzo-c-phenanthridine alkaloid salts can be used, as, for example the following:

| Chelerythrine chloride | 0.4% |
| ethanol, USP | 64.6% |
| zinc chloride | 35.0% |

EXAMPLE III

Another example of a useful preparation in the present invention is as follows:

| sanguinarine sulfate | 1.0% |
| glycerine | 69.0% |
| water | 30.0% |

EXAMPLE IV

A preparation that can be diluted with water to form a preparation useful for treating periodontal disease has the following ingredients:

| Sanguinarine chloride | 0.1% |
| Chelerythrine chloride | 0.4% |
| glycerine, USP | 64.0% |
| Zinc chloride | 35.0% |

EXAMPLE V

Another preparation to be used as a mouthrinse for treating periodontal disease has the following formulation:

|  | % w/w |
| --- | --- |
| Deionized Water | 82.250 |
| Zinc Chloride, U.S.P. | 0.200 |
| Glycerin | 3.500 |
| Sodium Saccharin, U.S.P. | 0.100 |
| SDA 38F Alcohol | 10.143 |
| Poloxamer 407 | 0.100 |
| Polysorbate 80 | 0.500 |
| Flavor | 0.207 |
| Solution of Example I | 3.000 |
| Total | 100.000 |

Sanguinarine chloride, chelerythrine chloride, and the other related benzo-c-phenanthridine alkaloids have strong antimicrobial properties, as can be seen from the following table:

| Microorganism | Mean inactivating dose of sanguinarine chloride in micrograms per milliliter of media |
| --- | --- |
| Bacillus subtilis | 22 |
| Escherichia coli | 270 |
| Klebsiella pneumoniae | 540 |
| Proteus vulgaris | 590 |
| Staphylococcus aureus | 70 |
| Streptococcus faecalis | 393 |
| Candida albicans | 150 |
| Saccharomyces cerevisiae | 20 |
| Pseudomonas aeruginosa | 7,000 |

It was further found that a concentration of sanguinarine chloride of 25 micrograms per milliliter caused a 100% reduction of dental plaque by inactivating plaque forming microorganisms freshly collected from human dental plaque. Sanguinarine chloride compared favorably in vitro with chlorhexidine, a material used as a standard in evaluating human dental plaque forming microorganisms.

A study was conducted to evaluate the effects on plaque and gingivitis of sanguinarine solutions when delivered through a ProPulse oral irrigator.

Lang, in J. Clin. Perio. 8:189–202 (1981), has reported on optimizing the dosage of chlorhexidine digluconate in clinical plaque control when applied by a Broxojet oral irrigator. It was found that one daily irrigator application of 400 ml. of 0.02% chlorhexidine solution was the optimal and lowest concentration for complete inhibition of plaque. Chlorhexidine has customarily been used as a rinsing solution of 0.2%, suggesting that the oral irrigator has a positive effect on chlorhexidine efficacy. Lang observed that the effects on gingivitis were similar to those on plaque.

This study was to determine if sanguinarine, which has been found to be an effective agent for controlling plaque, could be effective if delivered with an oral irrigator.

Thirteen subjects were enrolled in the study. Thee were five females and eight males who ranged in age from 21 to 39, with an average age of 29. They were informed of the purpose and intent of the study and consent forms were aligned.

All subjects received a through scaling and prophylaxis, and were instructed in optimal oral hygiene including toothbrushing and flossing. This phase of the study was continued for about two weeks or until the subjects presented themselves with a plaque-free dentition and clinically healthy gingivae.

On beginning the test phase, the subjects were given an irrigator and instructed in its use using the consumer supragingival irrigating tip. Plaque scoring was done by the method of Silness and Loe, *J. Perio.* 38:616–616, 1967, nd gingivitis by the method of Loe and Silness, *Acta. Odont. Scand.* 22:533–551, 1963. The subjects were randomized and given a prediluted rinse equivalent to 30 ml. of the formulation of the first example above in 370 ml. water, or 60 ml. of the formulation of the first example above in 340 ml. water. The test solution corresponded to 0.00225% sanguinarine (22.5 ug/ml) and 0.0090% sanguinarine (90 ug/ml) respectively. The subjects were instructed to irrigate with the test solutions twice daily on a setting of five for 14 days without any other oral hygiene and to present themselves on days 4, 7, and 14 for plaque scoring and gingivitis scoring. This constituted test phase I. At the end of test phase I the subjects were crossed over to the second test product after a two-week rest period that included optimal oral hygiene, scaling, and prophylaxis. The subjects begas test phase II and were scored at 0, 4, 7, and 14 days as before for plaque and gingivitis.

The rate of delivery of each test solution was determined before the study to insure that water and different rinse concentrations did not vary appreciably.

At the beginning of the study, plaque indices were zero and the gingivitis indices averaged 0.4 for the irrigating groups. When an oral rinse, the subjects' scores were zero for plaque and 0.17 for gingivitis at day 0. At day 4, the subjects supragintigally irrigating with 0.00225% sanguinaria had a mean plaque index (PI) of 0.37, at day 7 a mean PI of 0.56, and at day 14 a mean PI of 0.83. Similarly, the plaque scores for days 4, 7, and 14 for supragingival irrigation with 0.0090% sanguinarine were 0.29, 0.33, and 0.55, respectively. For the oral rinse, the scores were 0.37, 0.53, and 0.74 for days 4, 7, and 14. For the placebo group with scores were 0.68, 1.00, and 1.28 for days 4, 7, and 14. Even though the scores for the supragingival irrigation with 0.0090% sanguinarine were less than when irrigating with 0.0025% and when rinsing with 0.03% sanguinarine, there were no statistically significant differences among these groups.

For the mean gingivitis indices (GI) scores, the group on 0.030% sanguinarine rinse ranged from 0.33 at day 4 to 0.47 at day 7 and 0.79 at day 14. For the placebo rinse the scores were 0.65, 0.95, and 1.48 at days 4, 7, and 14. Supragingival irrigation with 0.0025% sanguinarine gave mean GI scores of 0.34, 0.42, and 0.67 at days 4, 7, and 14/ similarly, for 0.0090% sanguinarine supragingival irrigation, mean gingivitis scores of 0.25, 0.26, and 0.37 were recorded for days 4, 7, and 14.

The rate of delivery of each test solution through the irrigator at a setting of five was determined. The solution with 0.00225% sanguinarine was delivered at 430 ml/minute and the solution with 0.0090% sanguinarine was delivered at 444 ml/minute.

This study demonstrated that sanguinarine delivered supragingivally is effective in plaque and gingivitis control, but the effects are greatest when delivered via irrigation. The effects were also dependent upon the sanguinarine concentration of the irrigating solution.

Another study was conducted on fifteen subjects, eight males and seven females, ages 18–44 years and averaging 26 years of age, and having a gingival score of not less than 1.5. The subjects were entered into one of three groups for testing. On day 0 the subjects were given one of three test products consisting of either 0.00225% (22.5 ug/ml) sanguinarine in 400 ml water (product A), plain water (product B), or 0.03% sanguinarine oral rinse (product C). The subjects were instructed on how to supragingivally irrigate with products A and B using a ProPulse irrigate twice daily, and how to apply Product C with twice daily rinses with two 15 ml quantities each time. Subjects were scores at day 0, 7, and 14 for plaque index (PI) by the method of Quiqley and Hein, *J. Am. Dent. Assoc.* 65:26–29, 1962, and for gingival index (GI) by the method of Loe and Silness as described above. The products under test were the only oral hygiene allowed during the two week test phase. At the end of the two weeks, all subjects were given a complete dental prophylaxis and oral hygiene instruction of brushing and flossing.

None of the treatments produced large quantitative reductions in plaque. The reduction in gingivitis for product A was 70% compared to 57% for product B and 30% for product C.

In the treatment of periodontal disease according to the present invention, a jet stream of the dilute benzo-c-phenanthridine alkaloid solution is provided for application of the medication of the gingival tissues. The jet stream is provided by pumping the dilute solution through an orifice to provide a jet stream of the solution which is capable of penetrating directly into the periodontal pockets associated with periodontal disease.

In this regard, the jet steam provided should have characteristics such that upon application of the jet stream to the affected tissues, the aqueous solution of the jet stream will be forced into the periodontal pockets, thus providing fluid force access for delivering the aqueous benzo-c-phenanthridine salt solution into these pockets. Although jet streams of other characteristics may be capable of penetrating into periodontal pockets, it is generally satisfactory to pump the solution through a suitable orifice in order to provide a jet stream of the solution having a diameter of from about 0.3 mm to about 1.0 mm and an average flow rate of between about 250 cc/min. and about 600 cc/min. Furthermore, it is particularly preferred that the jet stream of benzo-c- phenanthridine salt solution be a pulsating jet stream such as provided by periodically varying the pumping rate and/or pressure so that the rate and force of delivery of the treatment solution to the affected tissues will vary rapidly with time. The jet stream should pulsate with a frequency of about 20 cycles per second and about 200 cycles per second. Furthermore, the relative amplitude of pulsation should be large, and in this regard it is desirable that during the intervals between the pulse peaks, which interval is ordinarily between about 20 percent and 40 percent of the pulse cycle time, that the flow of the jet stream be completely or almost completely interrupted.

It should be noted that when a course of treatment of periodontal disease is commenced, that the gums may be capable of tolerating the application of only a relatively weak jet stream of the treatment solution. As improvement progresses, the gums are increasingly capable of tolerating more intense and forceful jet streams of the treatment solution. Accordingly, the appropriate jet stream characteristics may be adjusted depending upon the stage of the periodontal disease, and more forceful jet streams may be applied as the patient's condition improves.

A suitable jet stream of treatment solution may be provided by conventional dental irrigating devices, such as those manufactured under the trade names Water-Pik and ProPulse, which are capable of ejecting pulsating jet streams of the treatment solution which are satisfactory for use in the present method. By employing such a commercially available dental irrigating device, treatment for periodontal disease according to the present invention may be conveniently self-administered on a regular basis.

In accordance with the present method, the dilute aqueous benzo-c-phanenthridine salt solution is applied by directing the pulsating jet stream of the solution against the diseased gingival tissues and into the periodontal pockets. The application of the jet stream solution into the periodontal pockets is readily accomplished by directing the stream toward the interdental spaces and along the inner and outer margins between the teeth and gums of both the upper and lower jaw, at an angle inclined toward the roots of the teeth. Playing the stream along these areas in a slow sweeping motion is a convenient and practical method of applying the medication to these regions.

Since the method may be self-administered by the patient, it may be periodically repeated in a relatively frequent manner. It is desirable that the procedure be repeated at least daily.

By applying the benzo-c-phenanthridine solution by means of an irrigation device capable of providing a pulsating jet stream, it is found that the cleansing, bactericidal, and bacteriostatic properties of the benzo-phenanthridine salts are all utilized in combination and to the fullest advantage toward the control and relief of the periodontal disease. The affected tissue, and particularly the periodontal pockets, are effectively cleansed of debris, including food, purulent discharges and other toxic matter, bacteria, and tissue debris, and a residue of bacteriocidal and bacteriostatic medication is left in place. Furthermore, it is believed that the medication is forced deep into normally inaccessible gingival and periodontal pockets which harbor the destructive infection in periodontal disease and which if not treated would perpetuate the progression of the pyorrheic process. By this means, infection in theses pockets can be reduced, with consequent reduction of the gum margins to permit better drainage of purulent secretions.

A particular advantage of using the benzo-c-phenanthridine alkaloid salts in the manner according to the present invention is the substantivity of these salts to oral tissues particularly to dental plaque. The salts are not easily washed away by the action of water or saliva, and thus are able to remain in the oral area to provide continuous bacteriostatic and bactericidal action.

What is claimed is:

1. A self-administerable method for the treatment and control of periodontal disease by supragingival irrigation comprising, pumping a dilute aqueous solution of a non-toxic benzo-c-phenanthridine alkaloid salt at concentrations from about 22.5 ug/ml to about 10 mg/ml through an orifice to provide a jet stream at a rate of 250 cc/minute to 600 cc/minute and a pulsation rate of 20 to 200 cycles per second penetrating directly into periodontal pockets associated with periodontal disease, and applying the jet stream of dilute benzo-c-phenanthridine alkaloid salt solution along the margins between the teeth and gums and into the periodontal pockets of an individual with periodontal disease so as to cleanse the diseased tissues and to provide a residue of said benzo-c-phenanthridine alkaloid salt.

2. The method of claim 1 wherein said benzo-c-phenanthridine alkaloid salt is selected from the group consisting of non-toxic salts of sanguinarine, chelerythrine, protopine, sanguirubine, sanguilutine, chelylutine, macarpine, hemochelidonene, and mixtures thereof.

3. The method of claim 2 wherein the salt is sanguinarine chloride.

4. The method of claim 1 wherein the salt is a mixture of sanguinarine chloride and chelerythrine chloride.

5. The method of claim 3 wherein the dilute aqueous solution includes zinc chloride.

6. The method of claim 1 wherein the jet stream of fluid is a pulsating stream.

7. The method of claim 1 wherein the jet stream flow is interrupted in an interval between pulse peaks.

* * * * *